United States Patent [19]

Bernardi

[11] Patent Number: 4,526,569
[45] Date of Patent: Jul. 2, 1985

[54] PORTABLE DEVICE FOR INFUSING INSULIN ON THE BASIS OF GLYCEMIC MEASUREMENTS

[76] Inventor: Luigi Bernardi, Via Renato Fucini 246, 00137 - Rome, Italy

[21] Appl. No.: 438,785

[22] Filed: Nov. 3, 1982

[30] Foreign Application Priority Data

Nov. 4, 1981 [IT] Italy .................................. 49638 A/81

[51] Int. Cl.³ ............................................. A61M 5/00
[52] U.S. Cl. ........................................ 604/4; 604/65; 604/31; 210/434
[58] Field of Search ................ 128/DIG. 3, DIG. 13, 128/632, 635; 604/4–6, 27–31, 43, 65–67, 269; 427/2, 4, 251; 210/498, 506–510, 434, 433.2, 927, 96.2

[56] References Cited

U.S. PATENT DOCUMENTS

| 3,579,441 | 5/1971 | Brown | 604/4 |
| 3,994,799 | 11/1976 | Yao et al. | 204/301 |
| 4,127,481 | 11/1978 | Malchesky | 210/22 A |
| 4,209,392 | 6/1980 | Wallace | 210/23 F |
| 4,253,456 | 3/1981 | Schindler | 128/214 R |
| 4,464,172 | 8/1984 | Lichtenstein | 128/DIG. 13 |

FOREIGN PATENT DOCUMENTS

| 7718736 | 6/1977 | Fed. Rep. of Germany . |
| 2737922 | 3/1979 | Fed. Rep. of Germany . |
| 2409741 | 6/1979 | France . |
| WO81/01794 | 7/1981 | PCT Int'l Appl. . |

OTHER PUBLICATIONS

Clemens, A. H., "Feedback Control Dynamics for Glucose Controlled Insulin Infusion System", Medical Progress Through Technology, vol. 6, pp. 91–98, (1979).

Goriya, Y. et al., "The Development of an Artificial Beta Cell System and Its Validation in Depancreatized Dogs: The Physiological Restoration of Blood Glucose Homeostasis", Medical Progress Through Technology, vol. 6, pp. 99–108, (1979).

Primary Examiner—C. Fred Rosenbaum
Assistant Examiner—Karen Kaechele
Attorney, Agent, or Firm—Bucknam and Archer

[57] ABSTRACT

The invention relates to a device made by a concentric dual lumen catheter, a pump, a small hemofilter, a glucose sensor which, by means of a microinfusion pump with a stepping motor controlled by a microprocessor can, through another concentric dual lumen catheter, inject insulin or glucose into the blood stream depending on glycemic levels.

10 Claims, 5 Drawing Figures

PORTABLE DEVICE FOR INFUSING INSULIN ON THE BASIS OF GLYCEMIC MEASUREMENTS

BACKGROUND OF THE INVENTION

This invention is referred to a device for diabetes treatment through the continual determination of glycemic levels and the automatic administration of insulin or glucose, eliminating the disadvantages of the only artificial pancreas now available, which subtracts blood from the patient, compelling him to bed.

There is in the market an apparatus under the commercial name of BIOSTATOR, produced by the LIFE SCIENCE DIVISION of MILES LABORATORIES, Elkhart, Ind., USA. It essentially consists of a glucose sensor, a system of insulin infusion and a computer which, through an appropriate algorithm, carries into effect the information of glycemic levels into an adequate administration of insulin (or glucose). A daily blood loss of nearly 50 ml, and the non-portability of the apparatus which compels the patient to bed as well as the brief duration (less than 50 hours) of the sensor due to progressive desensibilization are the obvious disadvantages of this system.

SUMMARY OF THE INVENTION

The device is made by a concentric dual lumen catheter, a pump, a hemofilter, a glucose sensor which, by means of a microinfusion pump with a stepping motor can, through another dual lumen concentric catheter, inject insulin or glucose into the bloodstream on the basis of the glycemic level. The object of the present invention exploits a new system: the blood, drawn through a dual lumen concentric catheter, is ultrafiltered and reinfused intravenously through a second catheter used also for the inlet of glucose or insulin when necessary; the ultrafiltrate thus obtained is then sent to the glucose sensor.

DESCRIPTION OF THE PREFERRED EMBODIMENT

Figure 1:
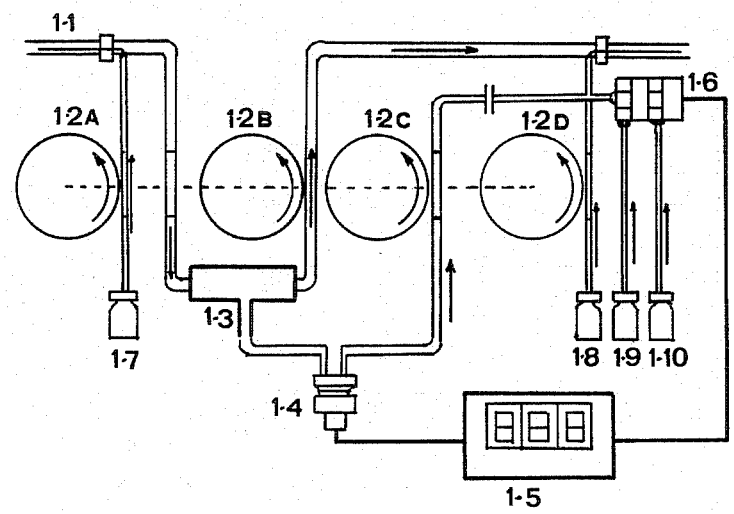
FIG. 1 is a schematic description of the device.

The main parts of the device are the following (FIG. 1):
1-1 concentric dual lumen intravenous catheter.
1-2 pump.
1-3 hemofilter.
1-4 glucose sensor.
1-5 display and control circuit.
1-6 insulin and glucose pump.
1-7 heparin tank.
1-8 physiological solution tank.
1-9 insulin tank.
1-10 glucose tank.

Figure 2:
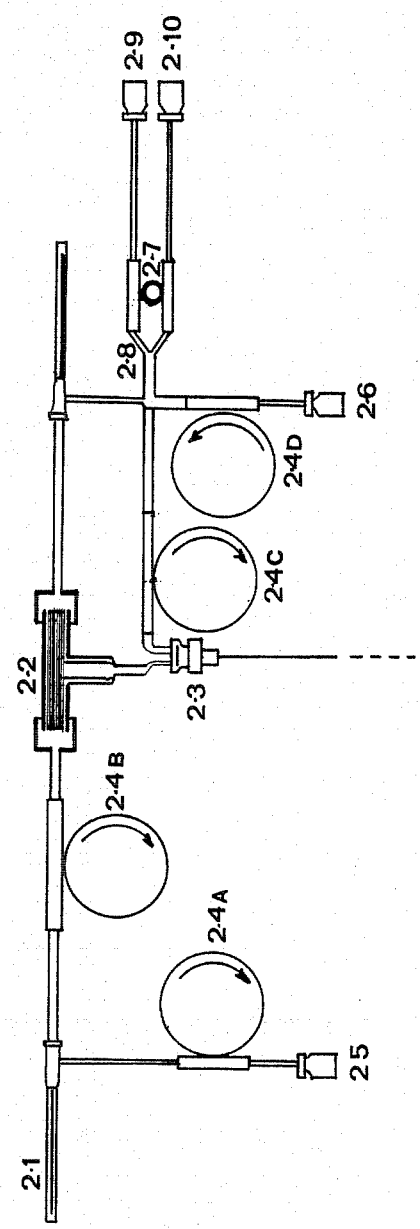
FIG. 2 is a scheme of the blood circuit.
Figure 3:
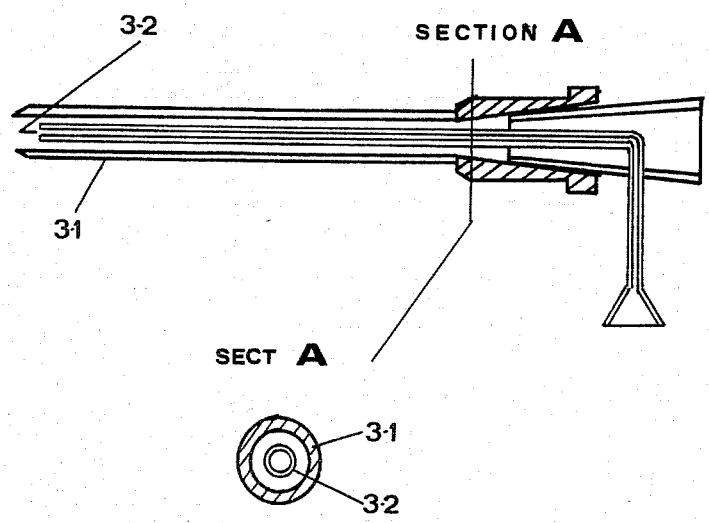
FIG. 3 is the concentric dual lumen catheter.

From the functional point of view the device can be divided on four parts:
A. Blood circuit.
B. Glycemic measurement.
C. Display—control circuit.
D. Infusion pump.
A. Blood circuit The blood is drawn from a vein through a teflon concentric dual lumen catheter (FIG. 2 and FIG. 3).

This catheter is made of a teflon needle (3-1) with inside a smaller needle (3-2). The internal needle carries the heparin to the blood flowing through the external needle in order to prevent coagulation. In the space which remains between the inserted needle and the enclosing bigger one the heparinated blood flows towards the filter system (2-2).

Figure 4:
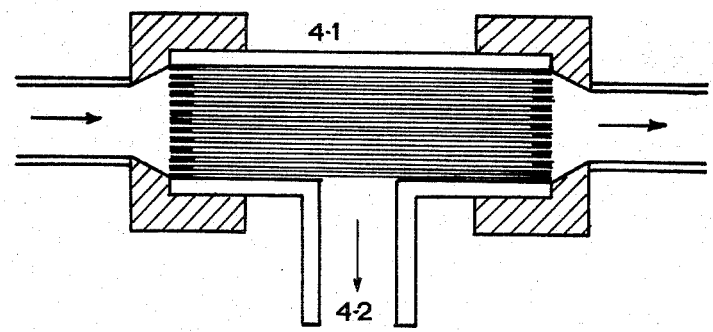
FIG. 4 is the filter system (scale 9:1).

The hemofilter (FIG. 4) is a hollow-fibers type. These fibers are permeable only to the small molecules. Therefore the cells, the proteins and the other macromolecules proceed downward proceed through the circuit, while the ultrafiltrate thus obtained, made of water and microsolutes, proceeds towards the glucose sensor (2-3). The filtered blood, having lost part of its water and microsolutes is obviously more concentrated than at the beginning of the operation. This blood will re-enter a vein through a second concentric dual lumen catheter equal to the introductory one. Here again the blood will flow through the interstice between the needles, while in the internal lumen flows the amount of physiological solution required to restore the correct hematocrit value. Through this same needle insulin or glucose can be introduced. The flowing of blood, heparin and physiological solution through all these circuits takes place by means of a multi-channel pump (2-4 a,b,c,d). The heparin and physiological solution are contained in special tanks (2-5 and 2-6).

B. Glycemic measurement

The glucose level is determined by analyzing the ultrafiltrate obtained from the hemofilter. As mentioned above, this ultrafiltrate runs from the filter towards the glucose sensor. The glucose sensor used in this system is of an enzymatic type combined with an amperometric system of measurement (the electrodes of the sensor supply a current directly proportioned to the blood glucose concentration). This type of sensor is used in the BIOSTATOR, but due to the passage of whole blood (even if heparinated) it loses sensibility after about 50 hours of operation, while with this system the absence of cells or elements of coagulation coming in contact with the surface of the sensor allows much longer period of sensitivity. After passing through the sensor the ultrafiltrate can either proceed to a small waste-pipe or be reinfused intravenously by the same way as the physiological solution.

C. Display—Control circuit

This part of the device is made of a microprocessor unit which controls the other parts by an interface.

The signal from the sensor is converted from analog to digital by a converter, then amplified. After amplification, the signal goes to the input port of the microprocessor, which stores the data and controls the display showing glycemic value. At this point, the microprocessor sends pulses by an appropriate algorithym to the insulin or glucose infusion pump.

D. Infusion pump

The acting part of the measurement system described above is the infusion pump (2-7).

This pump is moved by a stepping motor. This motor is made of two identical wirings assembled on the same axle, but operating in such a way that each one of the wirings move the axle in opposite directions. Exactly in view of this feature this motor can make the pump turn clock-wise or counter-clock-wise simply by switching the wirings. Hence this pump can infuse insulin when turning in one sense, or glucose while turning in the opposite sense. This motor was chosen also for its very high precision; in fact a constant amount of insulin or glucose is injected on every pulse sent by the microprocessor and one can control the quantity of insulin or glucose to infuse by selecting the number of given pulses.

Figure 5:
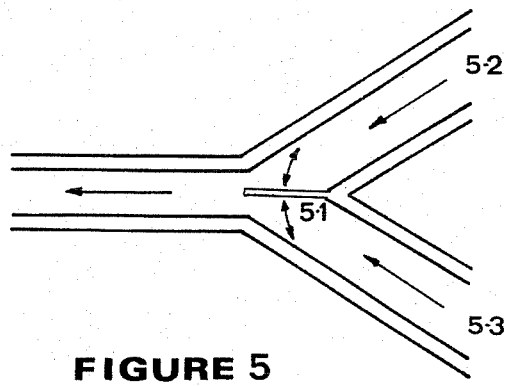
FIG. 5 is the valve for infusion of insulin or glucose.

The circuit is completed by a valve (FIG. 5) made of a plastic membrane (5-1) fixed to the bottom of the "Y" (2-8) formed by the conjunction of the insulin and glucose tubing (5-2 and 5-3); so when the pump rotates in one sense the pressure in one tube pushes the plastic membrane and the negative pressure of the other tube pulls the membrane, so that the second tube is closed and there is no reflux of solution.

I claim as my invention:

1. A portable device having a circuit for blood drawing and re-immission, said circuit comprising:
   (a) means for drawing blood from a patient into the circuit;
   (b) a filter connected to said means for drawing blood, said filter being permeable only to the water and microsolutes of the drawn blood such that said water and microsolutes pass through the filter whereas other constituents of the drawn blood including cells, proteins and other macromolecules do not pass through the filter;
   (c) a glucose sensor connected to said filter for receiving said water and microsolutes;
   (d) means for connecting said glucose sensor to said filter directly such that no substance other than said water and microsolutes flows between said filter and said glucose sensor;
   (e) a microprocessor connected to said glucose sensor which resonds to the glucose levels measured by said sensor by sending control signals; and
   (f) means connected to said microprocessor for infusing glucose and or insulin into the patient in response to said control signals received from the microprocessor.

2. The portable device of claim 1, wherein said filter is a hemofilter comprising hollow fibers.

3. The portable device of claim 1, further comprising means for infusing the cells, proteins and other macromolecules of the drawn blood back into the patient.

4. The portable device of claim 3, further comprising means for adjusting the hematocrit ratio of the cells, proteins, and other macromolecules before they are infused back into the patient.

5. The portable device of claim 4, wherein said means for adjusting said hematocrit ratio comprise a concentric dual lumen catheter with one lumen containing said cells, proteins, and other macromolecules and the other containing an amount of physiological solution required to provide an appropriate hematocrit value.

6. The portable device of claim 1, wherein said means for infusing insulin and/or glucose into the patient comprise a stepping motor, a pump, and a valve, said stepping motor acting on pulses received from said microprocessor to make the pump turn clockwise or counterclockwise to operate the valve to permit infusion of glucose or insulin into the patient.

7. The portable device of claim 6, wherein said means for infusing insulin and/or glucose into the patient comprise a "Y" shaped junction formed by the confluence of insulin and glucose tubing with the upper legs of the "Y" being respectively formed by an insulin carrying tube and a glucose carrying tube, and the lower leg of the "Y" being formed to carry either glucose or insulin into the patient, said valve comprising a plastic membrane fixed to the bottom of the intersection formed by said insulin carrying tube and said glucose carrying tube, said plastic membrane operating upon rotation of said pump to respectively open or close said insulin carrying tube or said glucose carrying tube.

8. The portable device of claim 5, further comprising means for reinfusing into the patient said water and microsolutes which have passed through said filter.

9. The portable device of claim 8, wherein said means for reinfusing into the patient said water and microsolutes comprise the concentric dual lumen catheter which forms part of said means for adjusting said hematocrit ratio.

10. The portable device of claim 9, wherein said means for infusing glucose and/or insulin into the patient comprise the concentric dual lumen catheter which forms part of said means for adjusting said hematocrit ratio.

* * * * *